United States Patent
Sternberg et al.

(10) Patent No.: US 10,016,775 B2
(45) Date of Patent: Jul. 10, 2018

(54) DEVICE FOR COATING A STENT AND ASSOCIATED COATING METHOD AND STENT PRODUCED ACCORDING TO THE METHOD

(71) Applicants: Katrin Sternberg, Rostock (DE); Heyo K. Kroemer, Neuenkirchen (DE); Klaus-Peter Schmitz, Warnemuende (DE); Werner Weitschies, Neuenkirchen (DE); Niels Grabow, Rostock (DE); Claus Harder, Uttenreuth (DE); Peter Littwin, Rostock (DE); Dailbor Bajer, Rostock (DE)

(72) Inventors: Katrin Sternberg, Rostock (DE); Heyo K. Kroemer, Neuenkirchen (DE); Klaus-Peter Schmitz, Warnemuende (DE); Werner Weitschies, Neuenkirchen (DE); Niels Grabow, Rostock (DE); Claus Harder, Uttenreuth (DE); Peter Littwin, Rostock (DE); Dailbor Bajer, Rostock (DE)

(73) Assignee: CORTRONIK GMBH, Rostock (DE)

( * ) Notice: Subject to any disclaimer, the term of this patent is extended or adjusted under 35 U.S.C. 154(b) by 802 days.

(21) Appl. No.: 14/370,928

(22) PCT Filed: Jan. 19, 2013

(86) PCT No.: PCT/EP2012/074818
§ 371 (c)(1),
(2) Date: Mar. 26, 2015

(87) PCT Pub. No.: WO2013/110393
PCT Pub. Date: Aug. 1, 2013

(65) Prior Publication Data
US 2015/0209813 A1 Jul. 30, 2015

Related U.S. Application Data

(60) Provisional application No. 61/589,409, filed on Jan. 23, 2012.

(51) Int. Cl.
*B05B 13/02* (2006.01)
*B05D 7/22* (2006.01)
*B05B 7/08* (2006.01)
*B05B 13/06* (2006.01)
*B05D 1/02* (2006.01)
*A61F 2/82* (2013.01)
*A61L 31/10* (2006.01)
*A61L 31/14* (2006.01)
*A61L 31/16* (2006.01)

(52) U.S. Cl.
CPC ............ *B05B 13/0221* (2013.01); *A61F 2/82* (2013.01); *A61L 31/10* (2013.01); *A61L 31/14* (2013.01); *A61L 31/16* (2013.01); *B05B 7/0815* (2013.01); *B05B 13/06* (2013.01); *B05D 1/02* (2013.01); *B05D 7/222* (2013.01); *A61F 2250/0067* (2013.01); *A61L 2300/21* (2013.01); *A61L 2300/216* (2013.01); *A61L 2300/412* (2013.01); *A61L 2300/432* (2013.01); *A61L 2300/606* (2013.01); *A61L 2420/02* (2013.01); *A61L 2420/04* (2013.01); *B05D 2254/02* (2013.01)

(58) Field of Classification Search
CPC .................. A61F 2/82; A61F 2/06; B32B 1/08
USPC ........... 623/1.15, 1.38, 1.46, 1.42; 428/34.1; 427/2.1, 230, 2.25
See application file for complete search history.

(56) References Cited

U.S. PATENT DOCUMENTS

| 2005/0238829 | A1* | 10/2005 | Motherwell | .......... B05B 7/0416 428/34.1 |
| 2007/0288088 | A1 | 12/2007 | Bureau et al. | |
| 2008/0226812 | A1 | 9/2008 | Chen | |
| 2010/0076544 | A1* | 3/2010 | Hoffmann | ............. A61L 31/022 623/1.15 |
| 2011/0073036 | A1 | 3/2011 | Tochterman et al. | |

FOREIGN PATENT DOCUMENTS

WO 2010120552 A2 10/2010

* cited by examiner

Primary Examiner — Dah-Wei D Yuan
Assistant Examiner — Andrew Bowman
(74) Attorney, Agent, or Firm — Greer, Burns & Crain, Ltd.; Steven P. Fallon

(57) ABSTRACT

A device for coating a stent, including a holder for the stent, a spraying unit comprising a spray mandrel and an air nozzle. The spray mandrel, the air nozzle and the holder are configured and disposed relative to each other such that the spray mandrel projects from one side into the stent during coating and the air nozzle projects into the stent from the opposing side. A method for coating a stent employs the device. Stents that can be obtained according to the method.

15 Claims, 3 Drawing Sheets

DEVICE FOR COATING A STENT AND ASSOCIATED COATING METHOD AND STENT PRODUCED ACCORDING TO THE METHOD

FIELD

The invention relates to a device for coating a stent, to a coating method carried out with the aid of the device, and to a stent produced according to the method.

BACKGROUND

Implants are being employed in a wide variety of forms in modern medical technology. They are used, for example, to support vessels, hollow organs and vein systems (endovascular implants, such as stents), to fasten and temporarily fix tissue implants and tissue transplantations, but also for orthopedic purposes, such as nails, plates or screws.

The implantation of stents has become established as one of the most effective therapeutic measures for the treatment of vascular diseases. Stents have the purpose of performing a stabilizing function in hollow organs of a patient. To this end, stents of conventional build have a filigree support structure made of metal struts, which is initially present in compressed form for introduction into the body and is expanded at the site of the application. One of the main application areas of such stents is to permanently or temporarily dilate and hold open vascular constrictions, particularly constrictions (stenoses) of the coronary blood vessels. In addition, aneurysm stents are also known, which are used primarily to seal the aneurysm. The support function is additionally provided.

Stents include a peripheral wall with sufficient load-bearing capacity to hold the constricted vessel open to the desired extent and a tubular base body through which the blood continues to flow without impairment. The peripheral wall is generally formed by a lattice-like supporting structure, which allows the stent to be introduced in a compressed state, in which it has a small outside diameter, all the way to the stenosis of the particular vessel to be treated and to be expanded there, for example by way of a balloon catheter, so that the vessel has the desired, enlarged inside diameter. As an alternative, shape memory materials such as nitinol have the ability to self-expand when a restoring force is eliminated that keeps the implant at a small diameter. The restoring force is generally applied to the material by a protective tube until the implant is released.

The implant, notably the stent, has a base body made of an implant material. An implant material is a non-living material, which is used for applications in medicine and interacts with biological systems. A basic prerequisite for the use of a material as implant material, which is in contact with the body environment when used as intended, is the body friendliness thereof (biocompatibility). Biocompatibility shall be understood to mean the ability of a material to evoke an appropriate tissue response in a specific application. This includes an adaptation of the chemical, physical, biological, and morphological surface properties of an implant to the recipient's tissue with the aim of a clinically desirable interaction. The biocompatibility of the implant material is also dependent on the temporal course of the response of the biosystem in which it is implanted. For example, irritations and inflammations occur in a relatively short time, which can lead to tissue changes. Depending on the properties of the implant material, biological systems thus react in different ways. According to the reaction of the biosystem, the implant materials can be divided into bioactive, bioinert and degradable, for example resorbable, materials.

Implant materials include polymers, metallic materials, and ceramic materials (as coatings, for example). Biocompatible metals and metal alloys for permanent implants include, for example, stainless steels (such as 316L), cobalt-based alloys (such as CoCrMo cast alloys, CoCrMo forge alloys, CoCrWNi forge alloys and CoCrNiMo forge alloys), technical pure titanium and titanium alloys (such as cp titanium, TiAl6V4 or TiAl6Nb7) and gold alloys. In the field of biocorrodible stents, the use of magnesium or technical pure iron as well as biocorrodible base alloys of the elements magnesium, iron, zinc, molybdenum, and tungsten are proposed.

Stents comprising a coating for the local release of an active agent (referred to as local drug delivery (LDD) systems) have been known for quite some time and are widely used in practice. The drug is intended to prevent restenosis and, in some cases, additionally support the healing process. To this end, it is favorable to provide the antiproliferative active agent for preventing restenosis essentially only abluminally, because then it is primarily eluted into the vessel wall, where it is to take effect. The intent is to largely prevent a delay of the healing process on the luminal side of the stent by the antiproliferative active agent. The healing process can additionally be promoted by an appropriate second active agent that is luminally coated. The combination of a luminal with an abluminal coating further has the advantage that a form-fitting coating can be achieved, which considerably increases the mechanical stability of the coating.

Local differentiation of the active agent release is done in part with the aid of active agent reservoirs that are arranged on the surface of the stent. In addition, stent variants are known in which only a purely abluminal coating made of polymer and the active agent is applied. Moreover, systems in which differing active agents are released from polymer coatings abluminally and luminally have been described. WO 2010/120552 A1 describes stents that have a coating thickness that differs luminally from that which is present abluminally. Stents are also coated for other reasons, for example so as to influence the corrosion behavior of biocorrodible implant materials.

A number of methods have become established in industry for coating stents with active agents and other materials, such as polymers serving as the carrier matrix or corrosion protection purposes. These include spray-coating based on carrier gases, ultrasonic spraying, rotary spraying and rolling, as well as methods based on ink jet printing.

US 2008/0226812 A1 describes a coating apparatus which is able to coat both the luminal (inside of the stent) and abluminal (outside of the stent) surfaces. This is done with the aid of an ink jet printer, wherein the stent is rotated during coating. The method can also be employed to applying coatings including several layers.

US 2007/0288088 A1 describes the coating of a stent by way of spray-coating, in which the stent is rotated and the nozzle is located at a distance of 6.5 mm from the stent.

US 2011/0073036 A1 describes a device for coating the luminal surface of a stent. The device includes a sleeve that accommodates the stent during the coating process, wherein the stent is seated flush against the inside of the sleeve. Spray-coating on the luminal side of the stent is carried out by way of a movably mounted spray mandrel, which is inserted into the sleeve provided with the stent.

The coating methods and apparatuses of the prior art have the disadvantage that the differentiated application of the coatings to the luminal and abluminal sides of the stent is not possible or difficult. In addition, separately applied luminal or abluminal coatings frequently have lower stability, so that they can become detached from the implant in an uncontrolled manner.

SUMMARY

A first aspect of the invention relates to the provision of a device for coating a stent, including a holder for the stent, a spraying unit with a spray mandrel and an air nozzle. The spray mandrel, the air nozzle and the holder are configured and disposed relative to each other such that the spray mandrel projects from one side into the stent during coating and the air nozzle projects into the stent from the opposing side.

A further aspect of the invention relates to the provision of a method for coating a stent, including the following steps:
a) holding the stent;
b) coating the luminal side of the stent by introducing a spray jet via a spray mandrel and an air flow via an air nozzle such that the spray jet is deflected radially outwardly by the air flow in a counterflow region;
c) displacing a position of the counterflow region relative to the stent by at least one of the measures selected from moving the stent, moving the spray mandrel, moving the air nozzle, regulating the spray jet and regulating the air flow.

DETAILED DESCRIPTION OF THE PREFERRED EMBODIMENTS

Figure 1:
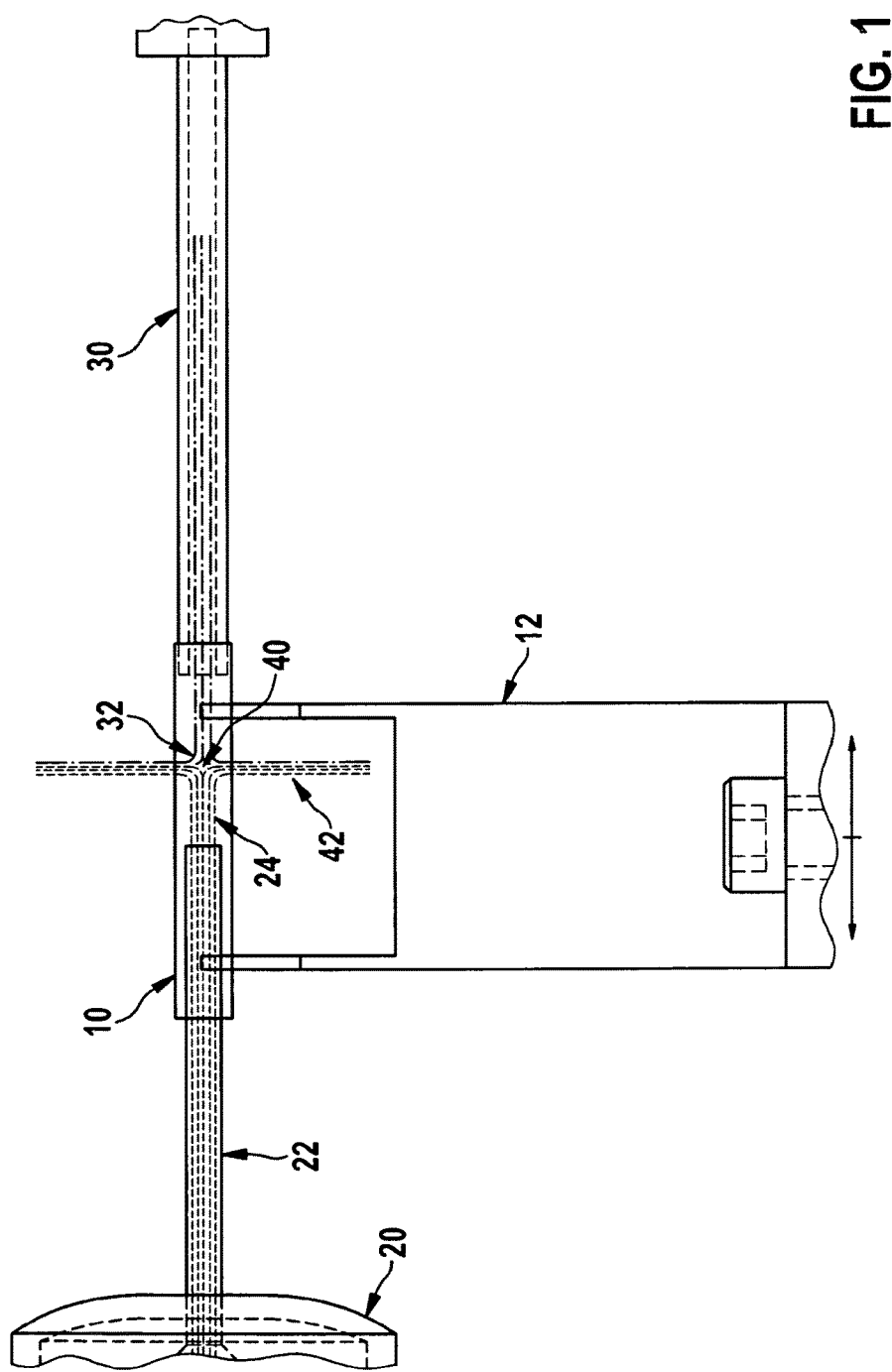
FIG. 1 is a schematic illustration of the device according to the invention for coating the luminal side of the stent.

The invention is based on the realization that luminal and/or abluminal coatings can be achieved in a very simple and reliable manner using a spraying method in which a counterflow is generated by an air nozzle. For this purpose, the device includes a spraying unit having a spray mandrel, the outside diameter of which is smaller than the inside diameter of the stent. Moreover, an air nozzle is present, the outside diameter of which likewise is smaller than the inside diameter of the stent. During the coating process, the stent is accommodated by a holder such that the lateral openings of the stent are accessible and the lateral walls are not shielded. The spray mandrel is then inserted into the stent from one side and the air nozzle from the opposing side.

During the coating process, a spray jet is generated by the spray mandrel and an air flow is directed at this spray jet by the air nozzle. In the region where the spray jet and air flow meet (which here is referred to as the counterflow region), the spray jet is deflected radially outwardly and thus coats the luminal surface of the stent in this region. Using different measures, it is now possible to vary the counterflow region relative to the position of the stent, whereby locally differentiated luminal coating of the stent is possible. These measures include moving the stent, the spray mandrel or the air nozzle and regulating the spray jet and air flow. The coating method according to the invention results in a form-fitting, mechanically very stable coating.

The device is preferably configured such that the position of the stent relative to the spray mandrel and the air nozzle can be varied during coating. The holder is notably configured such that, during coating, the stent can be moved in the direction of the spray mandrel or in the direction of the air nozzle. In other words, according to this variant the stent is moved along an axis formed by the spray mandrel and air nozzle via the holder during the coating process. The adjustments of the position and flow rate in the counterflow region can be determined in this region particularly easily by experiments and simplify the implementation of the method in the industrial manufacturing process.

It is further preferred for the spraying unit to include a spray nozzle, which is directed at an abluminal side of the stent. According to an associated variant of the method, in step a) a device for coating the stent is provided, in which the spraying unit includes such a spray nozzle, which is directed at an abluminal side of the stent. The abluminal coating can be carried out simultaneously with the aforementioned luminal coating (ii), before that (i) or (iii) thereafter. For simultaneously coating the abluminal side of the stent, a spray jet of the spray nozzle is directed at the counterflow region while steps b) and c) are carried out. Abluminal coating, however, can also be carried out before or after the luminal coating process, wherein a spray jet is directed at the outside of the stent. The quantity of coating material inadvertently reaching the luminal surface can optionally be reduced by an air flow from the air nozzle, or by a counterflow region, which is generated with an air nozzle and a spray mandrel that is operated without active agent.

In keeping with the aforementioned descriptions, according to this variant the spraying unit of the device according to the invention includes an additional spray nozzle, which is directed at the outside of the stent. Over the course of the abluminal coating step, the flow that is radially directed outwardly in the counterflow region can largely prevent coating material for the abluminal coating step from entering the interior of the stent. As an alternative or in addition, overpressure is generated in the interior of the stent with the spray mandrel or the air nozzle, this overpressure being intended to prevent penetration of the spray jet generated by the spray nozzle or to discharge penetrating material laterally.

During the abluminal coating step, the spray jet generated by the spray mandrel does not have to contain any carrier material or active agent, unless minor mixing is desirable for abluminal coating. The compositions of the coatings on the luminal and abluminal sides of the stent are generally different from each other, which is to say they include differing carrier materials and/or differing active agents. For example, growth-inhibiting active agents are preferably deposited on the abluminal upper face of the stent, while healing-promoting substances are applied to the luminal surface. The luminal and abluminal sides are preferably coated with differing active agents. In particular, atorvastatin is applied luminally and sirolimus is applied abluminally.

The active agents can notably be embedded in a carrier matrix. The carrier matrix can be biocorrodible and preferably includes PLLA.

A further aspect of the invention relates to a stent, which is produced according to the aforementioned method.

FIG. 1 schematically shows the principle of coating the luminal side of a stent 10 using the device according to the invention. For this purpose, the device includes a holder 12, which is used to accommodate the stent 10 during the coating process. The holder 12 is configured to perform a translatory movement by actuators, which are not shown in detail here.

The device further includes a spraying unit 20 having a spray mandrel 22. A spray jet 24 consisting of the coating material and a suitable carrier is generated by the spraying unit 20. The spray jet 24 is conducted into the interior of the stent 10 via the spray mandrel 22.

An air nozzle 30, which generates an air flow 32, is located on the opposite side of the stent.

The spray jet 24 and the air flow 32 meet in a counterflow region 40 and the spray jet 24—which is now mixed with the air flow 32—is accordingly directed radially outwardly and there impinges on the luminal surface of the stent 10 to be coated. A portion of this radially outwardly directed mixed flow 42 also enters through the openings of the filigree support structure of the stent 10.

So as to vary the location of the luminal coating, the holder 12 is moved along the axis formed by the spray mandrel 22 and air nozzle 30. The relative position of the counterflow region 40 to the stent 10 changes accordingly. In a certain luminal section of the stent 10, the composition of the luminal coating can be adjusted by varying the composition of the spray jet 24. The layer thickness can be influenced by the duration of the coating process and the coating composition in any arbitrary peripheral section of the luminal surface of the stent 10.

Figure 2:
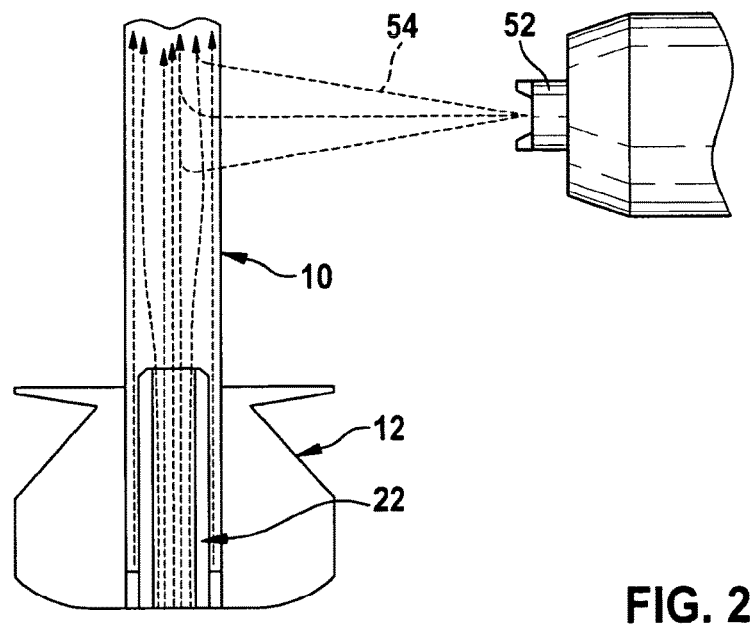
FIG. 2 is a schematic illustration of the device according to the invention for coating the abluminal side of the stent.

FIG. 2 is intended to illustrate a variant of the coating device in which the spraying unit includes an additional spray nozzle 52, which is used to coat the outside of the stent 10. A spray jet 54 is conducted over the stent 10 during the abluminal coating step by the spray nozzle 52. An overpressure, which effects an air flow that is directed radially outwardly through the filigree structures of the stent 10, can be generated in the interior of the stent 10 by the spray mandrel 22 and the air nozzle 30, which is not shown here. This air flow is adjusted so as to prevent penetration of the spray jet 54, while still allowing the abluminal surface of the stent 10 to be coated. Likewise, undesirable deposition of the abluminal layer material on the luminal surface can be reduced by way of an air flow that is generated by the air nozzle or spray mandrel.

Using the aforementioned device, a stent is first provided on the luminal side with a coating made of atorvastatin in PLLA and then on the abluminal side with a coating made of sirolimus in PLLA. The coating thickness on the inside of the stent should be approximately two to three times the coating thickness on the outside.

Figure 3:
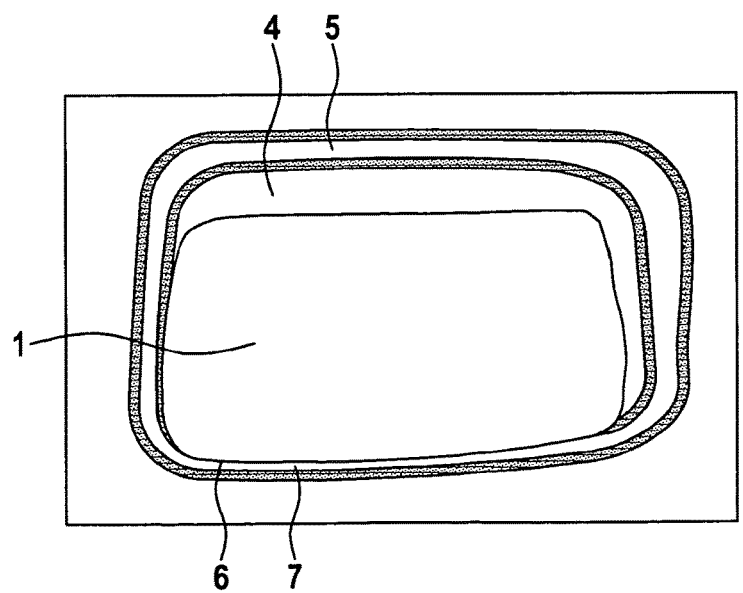
FIG. 3 is a schematic illustration of a transversally cut implant cross-section having a luminal and an abluminal layer thickness after sequentially combining separate inside and outside coatings.

FIG. 3 is a schematic illustration of a transversally cut implant cross-section having a luminal and an abluminal layer thickness after carrying out the sequential combination of separate inside and outside coatings.

The centers of the illustrations show the cross-section of a stent strut (1). The surface of the strut is surrounded by an inner layer (4, 6), wherein the luminal layer thickness (4) is considerably greater than the abluminal one (6). The abluminal layer thickness (6) is nonetheless greater than zero, resulting for the inner layer (4, 6) in both considerable accumulation on the luminal surface and in a form fit that increases the mechanical stability of the inner layer. The outer layer (5, 7) likewise exhibits form fit, wherein the abluminal layer thickness (7) is slightly less than the luminal one (5).

Figure 4:
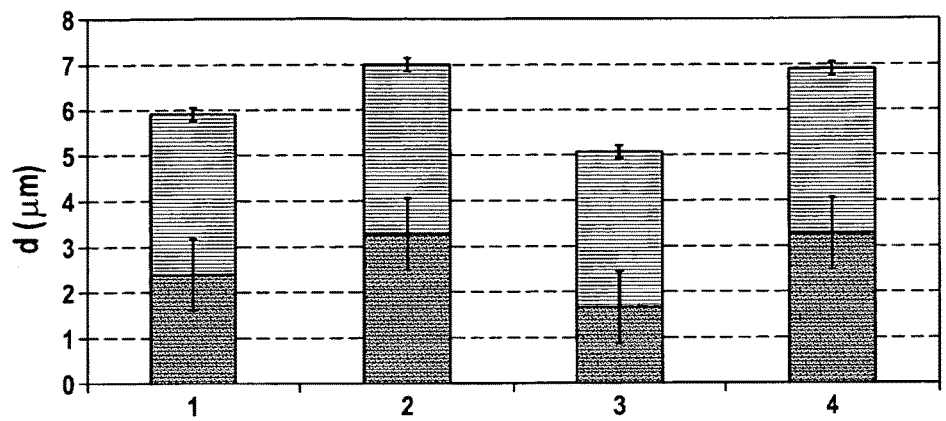
FIG. 4 is a layer thickness evaluation for the outside coatings of implant cross-sections in four transversal cutting planes for analysis of the longitudinal layer thickness consistency.
Figure 5:
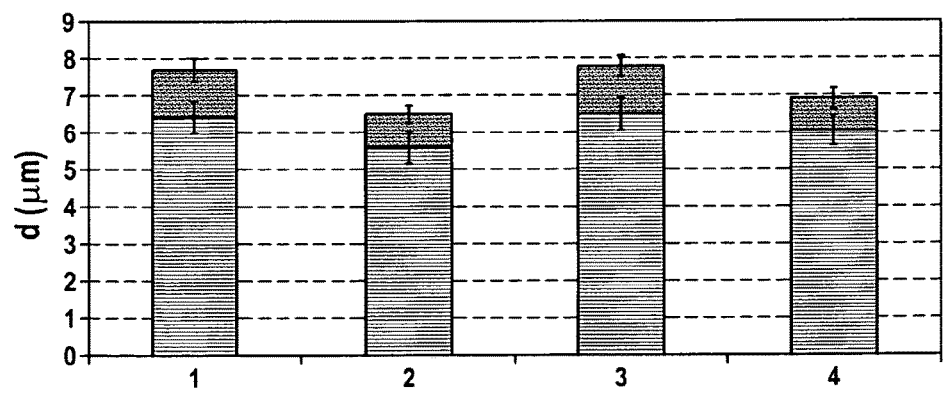
FIG. 5 is a layer thickness evaluation for the inside coatings of implant cross-sections in four transversal cutting planes for analysis of the longitudinal layer thickness consistency.

FIG. 4 shows a layer thickness evaluation for an outside coating and FIG. 5 shows a layer thickness evaluation for an inside coating of implant cross-sections in four transversal cutting planes for analyzing the longitudinal layer thickness consistency and the luminal/abluminal coating selectivity. Shown in light gray in FIG. 4 is the layer thickness of the layer material deposited on the abluminal implant surface, and shown in dark gray is the layer thickness of the layer material deposited on the luminal implant surface. Shown in light gray in FIG. 5 is the layer thickness of the layer material deposited on the luminal implant surface, and shown in dark gray is the layer thickness of the layer material deposited on the abluminal implant surface.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The invention claimed is:

1. A method for coating a stent, comprising the following steps:
   a) holding the stent in a holder that is part of a device including a spraying unit with a spray mandrel and an air nozzle, wherein the spray mandrel, the air nozzle and the holder are configured and disposed relative to each other such that the spray mandrel projects into the stent from one side during coating and the air nozzle projects into the stent from the opposing side, and wherein the stent can be moved in the direction of the spray mandrel or in the direction of the air nozzle during coating, and wherein the spraying unit further comprises a spray nozzle that is directed at an abluminal side of the stent;
   b) coating the luminal side of the stent by introducing a mandrel spray jet via the spray mandrel and an air flow via the air nozzle such that the spray jet is deflected radially outwardly by the air flow in a counterflow region;
   c) displacing a position of the counterflow region relative to the stent by at least one of the measures selected from moving the stent, moving the spray mandrel, moving the air nozzle, regulating the mandrel spray jet, and regulating the air flow; and
   d) while carrying out steps b) and c), a nozzle spray jet of the spray nozzle is directed at the counterflow region at the outside of the stent, wherein in the interior of the stent an air flow is generated by the air nozzle and the mandrel spray jet is simultaneously generated by the spray mandrel.

2. The method according to claim 1, wherein the luminal and abluminal sides are coated with differing active agents.

3. The method according to claim 2, wherein a healing-promoting active agent is applied to the luminal side.

4. The method according to claim 3, wherein the healing-promoting active agent is atorvastatin.

5. The method according to claim 2, wherein a proliferation-inhibiting active agent is applied to the abluminal side.

6. The method according to claim 5, wherein the proliferation-inhibiting active agent is sirolimus or a derivative thereof.

7. A method according to any one of claim 2, wherein the active agents are embedded in a carrier matrix.

8. The method according to claim 7, wherein the carrier matrix is biocorrodible.

9. The method according to claim 8, wherein the carrier matrix comprises PLLA.

10. A method for coating a stent, comprising the following steps: directing an axial spray jet with luminal coating material into the lumen of the stent; directing an opposite axial air flow into the lumen of the stent to meet the axial spray jet and create a counterflow region that redirects the axial spray jet radially outward to coat a luminal surface of the stent; simultaneously directing an abluminal spray jet with abluminal coating material to coat an abluminal surface of the stent, wherein the abluminal spray jet is aligned with the counterflow region to inhibit abluminal coating material from entering the lumen of the stent, and moving the counterflow region relative to the stent while maintaining alignment of the abluminal spray jet with the counterflow region.

11. The method of claim 10, further comprising creating an overpressure in the lumen of the stent.

12. The method of claim 10, wherein the luminal coating comprises a different active agent than the abluminal coating.

13. The method of claim 12, wherein the luminal coating comprises atorvastatin and the abluminal coating comprises sirolimus.

14. The method of claim 10, wherein the composition of the abluminal coating is adjusted during the moving.

15. The method of claim 10, wherein the duration of moving is varied to vary the thickness of the abluminal and luminal coatings in different peripheral sections of the stent.

* * * * *